US011147771B2

(12) United States Patent
Jaspart et al.

(10) Patent No.: US 11,147,771 B2
(45) Date of Patent: *Oct. 19, 2021

(54) ORODISPERSIBLE DOSAGE UNIT CONTAINING AN ESTETROL COMPONENT

(71) Applicant: ESTETRA SPRL, Liège (BE)

(72) Inventors: Séverine Francine Isabelle Jaspart, Bois-et-Borsu (BE); Johannes Jan Platteeuw, Boxtel (NL); Denny Johan Marijn Van Den Heuvel, Beuningen (NL)

(73) Assignee: ESTETRA SPRL, Liège (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/737,227

(22) PCT Filed: Jun. 17, 2016

(86) PCT No.: PCT/EP2016/064065
§ 371 (c)(1),
(2) Date: Dec. 15, 2017

(87) PCT Pub. No.: WO2016/203006
PCT Pub. Date: Dec. 22, 2016

(65) Prior Publication Data
US 2018/0169022 A1 Jun. 21, 2018

(30) Foreign Application Priority Data
Jun. 18, 2015 (EP) .................................... 15172767

(51) Int. Cl.
A61K 9/20 (2006.01)
A61K 9/00 (2006.01)
A61K 31/565 (2006.01)
A61K 9/16 (2006.01)
A61P 5/00 (2006.01)
A61P 15/18 (2006.01)

(52) U.S. Cl.
CPC .......... *A61K 9/2095* (2013.01); *A61K 9/0056* (2013.01); *A61K 9/2027* (2013.01); *A61K 9/2054* (2013.01); *A61K 9/2059* (2013.01); *A61K 9/2077* (2013.01); *A61K 31/565* (2013.01); *A61P 5/00* (2018.01); *A61P 15/18* (2018.01); *A61K 9/1623* (2013.01)

(58) Field of Classification Search
CPC ............................ A61K 9/2095; A61K 9/0056
See application file for complete search history.

(56) References Cited

U.S. PATENT DOCUMENTS

| | | | |
|---|---|---|---|
| 3,138,588 A | 6/1964 | Smith | |
| 3,433,785 A | 3/1969 | Philips et al. | |
| 5,164,405 A | 11/1992 | McFarlane et al. | |
| 5,340,586 A | 8/1994 | Pike et al. | |
| 6,117,446 A | 9/2000 | Place | |
| 6,723,348 B2 | 4/2004 | Faham et al. | |
| 6,992,218 B2 | 1/2006 | Dietlin et al. | |
| 7,723,320 B2 | 5/2010 | Bunschoten et al. | |
| 7,732,430 B2 | 6/2010 | Bunschoten et al. | |
| 7,871,995 B2 | 1/2011 | Bunschoten et al. | |
| 8,048,869 B2 | 1/2011 | Bunschoten et al. | |
| 7,923,440 B2 | 4/2011 | Bunschoten et al. | |
| 7,943,604 B2 | 5/2011 | Coelingh Bennink et al. | |
| 8,026,228 B2 | 9/2011 | Coelingh Bennink et al. | |
| 8,236,785 B2 | 8/2012 | Coelingh Bennink et al. | |
| 8,367,647 B2 | 5/2013 | Coelingh Bennink et al. | |
| 8,518,923 B2 | 8/2013 | Visser et al. | |
| 8,987,240 B2 | 3/2015 | Coelingh Bennink et al. | |
| 8,987,484 B2 | 3/2015 | Pascal | |
| 9,034,854 B2 | 5/2015 | Coelingh Bennink et al. | |
| 9,040,509 B2 | 5/2015 | Coelingh Bennink et al. | |
| 9,238,035 B2 | 1/2016 | Foidart et al. | |
| 9,561,238 B2 | 2/2017 | Coelingh Bennink et al. | |
| 9,579,329 B2 | 2/2017 | Wouters et al. | |
| 9,603,860 B2 | 3/2017 | Perrin | |
| 9,884,064 B2 | 2/2018 | Platteeuw et al. | |

(Continued)

FOREIGN PATENT DOCUMENTS

| | | |
|---|---|---|
| CL | 200501207 | 5/2005 |
| CL | 201400802 | 4/2014 |

(Continued)

OTHER PUBLICATIONS

Bianchi, "Estertrol: Desde Un Estrogeno Fetal Hasta El Tratamiento De La Menopausia," Rev. Chil. Obstet. Ginecol., vol. 74, No. 2, pp. 123-126 (2009).
Office Action dated May 1, 2019 in U.S. Appl. No. 15/737,233 (US 2018-0185271).
Office Action dated May 17, 2019 in U.S. Appl. No. 15/737,189 (US 2018-0153801).
Bennink et al., "Ovulation inhibition by estetrol in an in vivo model," Contraception 2008, vol. 77, pp. 186-190.
Gardouh et al., "Preparation and Characterization of Mucoadhesive Buccal Film for Delivery of Meloxicam," British Journal of Pharmaceutical Research, vol. 3, No. 4, pp. 743-766 (Jun. 2013).

(Continued)

Primary Examiner — Gina C Justice
(74) Attorney, Agent, or Firm — Foley & Lardner LLP

(57) ABSTRACT

The invention provides an orodispersible solid pharmaceutical dosage unit having a weight between 30 and 1,000 mg, said dosage unit consisting of: 0.1-25 wt. % of estetrol particles containing at least 80 wt. % of an estetrol component selected from estetrol, estetrol esters and combinations thereof; and 75-99.9 wt. % of one or more pharmaceutically acceptable ingredients; the solid dosage unit comprising at least 100 μg of the estetrol component; and wherein the solid dosage unit can be obtained by a process comprising wet granulation of estetrol particles having a volume weighted average particle size of 2 μm to 50 μm. The solid dosage unit is easy to manufacture and perfectly suited for sublingual, buccal or sublabial administration.

22 Claims, 1 Drawing Sheet

(56) References Cited

U.S. PATENT DOCUMENTS

| | | |
|---|---|---|
| 9,987,287 B2 | 6/2018 | Platteeuw et al. |
| 9,988,417 B2 | 6/2018 | Ferreiro Gil et al. |
| 10,000,524 B2 | 6/2018 | Verhaar et al. |
| 10,179,140 B2 | 1/2019 | Perrin et al. |
| 10,201,611 B2 | 2/2019 | Bennink et al. |
| 2002/0132801 A1 | 9/2002 | Heil et al. |
| 2004/0009960 A1 | 1/2004 | Heil et al. |
| 2004/0192620 A1 | 9/2004 | Bunschoten et al. |
| 2004/0198671 A1 | 10/2004 | Bunschoten et al. |
| 2005/0032755 A1 | 2/2005 | Van Look et al. |
| 2005/0070488 A1 | 3/2005 | Coelingh Bennik et al. |
| 2005/0147670 A1* | 7/2005 | Hsu ............... A61K 9/0056 424/464 |
| 2006/0063723 A1 | 3/2006 | Coelingh Bennink et al. |
| 2006/0211669 A1 | 9/2006 | Verhaar et al. |
| 2006/0276414 A1 | 12/2006 | Coelingh Bennink et al. |
| 2007/0048369 A1 | 3/2007 | Foreman et al. |
| 2007/0286819 A1 | 12/2007 | Devries et al. |
| 2007/0286829 A1 | 12/2007 | Batista |
| 2008/0113953 A1 | 6/2008 | DeVries |
| 2008/0166406 A1 | 7/2008 | Kristjansson |
| 2010/0035987 A1 | 2/2010 | Mang et al. |
| 2010/0093679 A1 | 4/2010 | Heil |
| 2011/0250272 A1 | 10/2011 | Besse et al. |
| 2011/0250274 A1 | 10/2011 | Shaked et al. |
| 2012/0077888 A1 | 3/2012 | Ramtoola et al. |
| 2012/0128733 A1 | 5/2012 | Perrin et al. |
| 2012/0220556 A1 | 8/2012 | Heil |
| 2013/0079400 A1 | 3/2013 | Riedl et al. |
| 2014/0083639 A1 | 3/2014 | Bonini et al. |
| 2014/0107091 A1 | 4/2014 | Pascal |
| 2014/0107358 A1 | 4/2014 | Pascal |
| 2014/0235882 A1 | 8/2014 | Platteeuw et al. |
| 2015/0045300 A1 | 2/2015 | Ahuja et al. |
| 2015/0133413 A1 | 5/2015 | Coelingh Bennink et al. |
| 2015/0182540 A1 | 7/2015 | Heil et al. |
| 2016/0101116 A1 | 4/2016 | Foidart et al. |
| 2016/0310506 A1 | 10/2016 | Platteeuw et al. |
| 2016/0367567 A1 | 12/2016 | Jaspart et al. |
| 2017/0196886 A1 | 7/2017 | Wouters |
| 2017/0216318 A1 | 8/2017 | Perrin et al. |
| 2017/0369521 A1 | 12/2017 | Platteeuw et al. |
| 2018/0153801 A1 | 6/2018 | Jaspart et al. |
| 2018/0185271 A1 | 7/2018 | Jaspart et al. |
| 2018/0265540 A1 | 9/2018 | Verhaar et al. |
| 2019/0125759 A1 | 5/2019 | Jaspart et al. |
| 2019/0167700 A1 | 6/2019 | Jost et al. |
| 2020/0046729 A1 | 2/2020 | Jost et al. |

FOREIGN PATENT DOCUMENTS

| | | |
|---|---|---|
| CN | 1197387 A | 10/1998 |
| CN | 1780634 A | 5/2006 |
| CN | 101443015 A | 6/2007 |
| CN | 101541326 A | 9/2009 |
| CN | 101631536 A | 1/2010 |
| CN | 101780073 A | 7/2010 |
| CN | 102058604 A | 5/2018 |
| DE | 20 2009 018 024 U1 | 1/2011 |
| EP | 0 371 466 A1 | 6/1990 |
| EP | 0 646 592 A | 5/1995 |
| EP | 20010201896 | 11/2002 |
| EP | 3046928 B1 | 7/2016 |
| EP | 3106148 A1 | 12/2016 |
| JP | 2002-508330 A | 3/2002 |
| JP | 2005-523283 T | 8/2005 |
| JP | 2009-256344 A | 11/2009 |
| JP | 2010-513514 T | 4/2010 |
| JP | 2012-240917 A | 12/2012 |
| JP | 2014-224079 A | 12/2014 |
| JP | 2018-165263 A | 10/2018 |
| WO | WO-95/02408 A1 | 1/1995 |
| WO | WO-95/17895 | 7/1995 |
| WO | WO-99/30728 A1 | 6/1999 |
| WO | WO-00/42942 | 7/2000 |
| WO | WO-00/42955 A1 | 7/2000 |
| WO | WO-01/05806 | 1/2001 |
| WO | WO-2001/040255 | 7/2001 |
| WO | WO-2002/49675 | 6/2002 |
| WO | WO-02/094275 A1 | 11/2002 |
| WO | WO-02/094276 A1 | 11/2002 |
| WO | WO-02/094277 A1 | 11/2002 |
| WO | WO-02/094278 A1 | 11/2002 |
| WO | WO-02/094279 A1 | 11/2002 |
| WO | WO-03/018026 A1 | 3/2003 |
| WO | WO-03018026 A1 | 3/2003 |
| WO | WO-2003018026 | 3/2003 |
| WO | WO-03/041718 A1 | 5/2003 |
| WO | WO-2004/006936 A1 | 1/2004 |
| WO | WO-2004/019954 | 3/2004 |
| WO | WO-2004/041289 | 5/2004 |
| WO | WO-2004/096259 | 11/2004 |
| WO | WO-2004/103377 A1 | 12/2004 |
| WO | WO-2005/030175 | 4/2005 |
| WO | WO-2005/030176 | 4/2005 |
| WO | WO-2005/051400 | 7/2005 |
| WO | WO-2005/105103 | 11/2005 |
| WO | WO-2005115349 | 12/2005 |
| WO | WO-2005115351 | 12/2005 |
| WO | WO-2006/002937 | 1/2006 |
| WO | WO-2006/027347 | 3/2006 |
| WO | WO-2006/125800 | 11/2006 |
| WO | WO-2006120035 | 11/2006 |
| WO | WO-2007/081206 | 7/2007 |
| WO | WO-2007/106264 | 9/2007 |
| WO | WO-2008/003363 | 1/2008 |
| WO | WO-2008/003432 | 1/2008 |
| WO | WO-2008/156365 | 12/2008 |
| WO | WO-2010/012490 A1 | 2/2010 |
| WO | WO-2010/033832 A2 | 3/2010 |
| WO | WO-2010089078 A1 | 8/2010 |
| WO | WO-2010/149273 | 12/2010 |
| WO | WO-2011/128336 | 10/2011 |
| WO | WO-2012/000981 | 1/2012 |
| WO | WO-2012/055840 | 5/2012 |
| WO | WO-2013012326 A1 | 1/2013 |
| WO | WO-2013/021025 A1 | 2/2013 |
| WO | WO-2013/090117 | 6/2013 |
| WO | WO-2014/159377 A1 | 10/2014 |
| WO | WO-2014/189836 | 11/2014 |
| WO | WO-2015/040051 | 3/2015 |
| WO | WO-2015/086643 A1 | 6/2015 |
| WO | WO-2016/053946 | 4/2016 |
| WO | WO-2016/187269 | 11/2016 |
| WO | WO-2016/203009 A1 | 12/2016 |
| WO | WO-2016/203011 | 12/2016 |
| WO | WO-2016/203044 A1 | 12/2016 |
| WO | WO-2016/207298 | 12/2016 |
| WO | WO-2016203006 | 12/2016 |
| WO | WO-2018/024912 | 2/2018 |
| WO | WO-2018/065076 | 4/2018 |
| WO | WO-2019/154899 | 8/2019 |

OTHER PUBLICATIONS

Haque et al., "Development of polymer-bound fast-dissolving metformin buccal film with disintegrants," International Journal of Nanomedicine, vol. 10 (Suppl. I: Challenges in biomaterials research) pp. 199-205 (Oct. 2015).

International Search Report issued in International Patent Application No. PCT/EP2014/077127, dated Feb. 3, 2015.

Notice of Allowance dated Aug. 15, 2019 in U.S. Appl. No. 16/025,719 (US 2019-0125759 A1).

Office Action (Advisory Action) dated Apr. 13, 2018 in U.S. Appl. No. 15/185,337 (US 2016-0367567 A1).

Office Action dated Jan. 3, 2018 in U.S. Appl. No. 15/185,337 (US 2016-0367567 A1).

Office Action dated Jul. 3, 2017 in U.S. Appl. No. 15/185,337 (US 2016-0367567 A1).

Office Action dated Mar. 28, 2019 in U.S. Appl. No. 16/025,719 (US 2019-015759 A1).

Office Action dated Nov. 4, 2019, in U.S. Appl. No. 15/737,233 (US 2018-0185271).

(56) References Cited

OTHER PUBLICATIONS

Office Action issued on Dec. 2, 2019 in U.S. Appl. No. 15/737,189 (US 2018-0153801).
Visser et al., "Clinical applications for estetrol," Journal of Steroid Biochemistry and Molecular Biology 114 (2009) 85-59.
Luo Lianmei et al., Major research advances in estetrol. J Reprod Med, vol. 18(3), pp. 305-308, Dec. 31, 2009.
Savjani et al, "Drug solubility: importance and enhancement techniques", ISRN Pharm., 2012: 195727, Jul. 5, 2012.
Williams et al., Strategies to address low drug solubility in discovery and development, Pharmacological Reviews, vol. 65(1), pp. 416-445, Jan. 1, 2013.
Anderson et al., Effects of conjugated equine estrogen in postmenopausal women with hysterectomy: the Women's Health Initiative randomized controlled trial, JAMA, vol. 291(14), pp. 1701-1712, Apr. 1, 2004.
Archer et al., A randomized, double-blind, placebo-controlled study of the lowest effective dose of drospirenone with 17β-estradiol for moderate to severe vasomotor symptoms in postmenopausal women, Menopause, vol. 21(3), pp. 227-235, Mar. 1, 2014.
Bjarnason et al., Acute and long-term estradiol kinetics in smoking postmenopausal women, Climacteric, vol. 15(5), pp. 449-454, Oct. 1, 2012.
Bosworth et al., Depressive symptoms, menopausal status, and climacteric symptoms in women at midlife, Psychosom Med., 63(4):603-8, Jul.-Aug. 2001.
Coelingh Bennink Herjan J T et al, Clinical effects of the fetal estrogen estetrol in a multiple-rising-dose study in postmenopausal women, Maturitas, Elsevier, Amsterdam, NL vol. 91, pp. 93-100, XP029649879, Jun. 23, 2016.
Harlow et al., Executive summary of the Stages of Reproductive Aging Workshop + 10: addressing the unfinished agenda of staging reproductive aging, Menopause, vol. 19(4), Apr. 1, 2012.
Heinemann et al., International versions of the Menopause Rating Scale (MRS), Health Qual Life Outcomes, pp. 1:28, Jul. 30, 2003.
Heinemann et al., The Menopause Rating Scale (MRS) scale: A methodological review, Health Qual Life Outcomes, pp. 2:45, Sep. 2, 2004.
Heinemann et al., The Menopause Rating Scale (MRS) as outcome measure for hormone treatment? A validation study, Health Qual Life Outcomes, pp. 2:67, Oct. 22, 2004.
Hilditch et al., A menopause specific quality of life questionnaire: development and psychometric properties, Maturitas, vol. 24(3), pp. 161-175, Jul. 1, 1996.
Notelovitz et al., Initial 17β-Estradiol Dose for Treating Vasomotor Symptoms, Obstetrics and Gynaecology, vol. 95(5), pp. 726-731, May 1, 2000.
Portman et al., Genitourinary syndrome of menopause: new terminology for vulvovaginal atrophy from the International Society for the Study of Women's Sexual Health and the North American Menopause Society, Menopause, vol. 21(10), pp. 1063-1068, Oct. 1, 2014.
Rodstrom et al., A longitudinal study of the treatment of 25 hot flushes: the population study of women in Gothenburg during a quarter of a century, Menopause, vol. 9(3), pp. 156-161, May-Jun. 2002.
Santoro, Symptoms of menopause: hot flushes, Clin Obstet Gynecol, vol. 51(3), pp. 539-548, Sep. 1, 2008.
Simon et al., Menopausal hormone therapy for vasomotor symptoms: balancing the risks and benefits with ultra-low doses of estrogen, Expert Opin Investig Drugs, vol. 16(12), pp. 2005-2020, Dec. 1, 2007.
Utian et al., Comparative controlled trial of a novel oral estrogen therapy, estradiol acetate, for relief of menopause symptoms, Menopause, vol. 12(6), pp. 708-715, Oct. 8, 2005.
Visser and Bennink, Clinical applications for estetrol, Journal of Steroid Biochemistry and Molecular Biology 114, pp. 85-89, 2009.
Bennink et al., Pharmacokinetics of the fetal estrogen estetrol in a multiple-rising-dose study in postmenopausal women, Climacteric. 20(3), pp. 285-289, Mar. 7, 2017.
Bennink et al., Pharmacodynamic effects of the fetal estrogen estetrol in postmenopausal women: results from a multiple-rising-dose study, Menopause 24(6), pp. 677-685, Jun. 1, 2017.
Dinger et al., *Effectiveness of Oral Contraceptive Pills in a Large U.S. Cohort Comparing Progestogen and Regimen*, Obstet. & Gynecol., 117(1):33-40, Jan. 1, 2011.
Dinger et al., *Oral Contraceptive Effectiveness According to Body Mass Index, Weight, Age, and Other Factors*, Am. J. Obstet. Gynecol., 201:263e1-9, Sep. 1, 2009.
Duijkers et al., *A randomized study comparing the effect on Ovarian activity of a progestogen-only pill (POP) containing desogestrel and a new POP containing drospirenone in a 24/4 regimen*, Euro. J. Contracept. & Repro. Health Care, 20(6):419-27, Jun. 15, 2015.
Elger et al., *Conception and pharmacodynamics profile of drospirenone*, Steriods, 68(10):891-905, Nov. 11, 2003.
Rosenbaum et al., *Inhibition of ovulation by a novel progestogen (drospirenone) alone or in combination with ethinylestradiol*, Euro. J. Contracept. & Repro. Health Care, 5(1):14-24, Mar. 1, 2000.
Al-Jefout et al., "Continuous Norethisterone Acetate versus Cyclical Drospirenone 3 mg/Ethinyl Estradiol 20 ug for the Management of Primary Dysmenorrhea in Young Adult Women," Journal of Pediatric and Adolescent Gynecology, vol. 29, No. 2, pp. 143-147, XP029421056, Sep. 3, 2015.
Andersch and Milsom: "An epidemiologic study of young women with dysmenorrhea", Am J Obstet Gynecol, 144(6), p. 655-660, Nov. 15, 1982.
Apter et al: "Bleeding pattern and cycle control with estetrol-containing combined oral contraceptives: results from a phase II, randomised, dose-finding study (FIESTA)", Contraception, 94(4), p. 366-373, Oct. 2016.
Arnal et al., "Tissue specificity of the membrane vs nuclear actions of estrogen receptor alpha: insights from targeted mutations in mouse models," Archives of Cardiovascular Diseases Supplements, (Apr. 2016) vol. 8(3), p. 217, Abstract 0333, Apr. 1, 2016.
Bagot et al: "The effect of estrone on thrombin generation may explain the different thrombotic risk between oral and transdermal hormone replacement therapy", J Thromb Haemost., 8(8):1736-1744 , Aug. 1, 2010.
Bennink et al., "Estetrol review: profile and potential clinical applications," Climacteric vol. 11, Suppl. 1, pp. 47-58, XP009194877 , Jul. 3, 2009.
Callejo et al: "Effect of a low-dose oral contraceptive containing 20 microg ethinylestradiol and 150 microg desogestrel on dysmenorrhea", Contraception, 68(3), p. 183-188, Sep. 1, 2003.
Dahlback et al: "Familial thrombophilia due to a previously unrecognized mechanism characterized by poor anticoagulant response to activated protein C: prediction of a cofactor to activated protein C", Proc Natl Acad Sci U S A., 90(3), p. 1004-1008, Feb. 1, 1993.
Davis et al: "Oral contraceptives for dysmenorrhea in adolescent girls: a randomized trial", Obstet Gynaecol, 106(1): 97-104 , Jul. 1, 2005.
De Bastos et al: "Combined oral contraceptives: venous thrombosis", Cochrane Database Syst Rev, (3):CD010813, Mar. 3, 2014.
Duijkers et al: "Inhibition of ovulation by administration of estetrol in combination with drospirenone or levonorgestrel: Results of a phase II dose-finding pilot study", Eur J Contracept Reprod Health Care,.20(6), p. 476-489, Aug. 20, 2015.
Endrikat et al: "A twelve-month comparative clinical investigation of two low-dose oral contraceptives containing 20 micrograms ethinylestradiol/75 micrograms gestodene and 20 micrograms ethinylestradiol/150 micrograms desogestrel, with respect to efficacy, cycle control and tolerance", Contraception, 52(4), p. 229-235, Oct. 1, 1995.
Foidart, "Estelle®, Estetrol and drospirenone in oral contraception: E4 Freedom TM Phase 3 clinical study design," Presented at Eur. Soc. Contraception & Reprod. Health, 14th Cong, 2nd Global Conf., May 7, 2016.
Foidart, "Estetrol, the first human, physiological Selective Estrogen Receptor Modulator," Presented at Eur. Soc. Contraception & Reprod. Health, 14th Cong, 2nd Global Conf. , May 8, 2016.
French: "Dysmenorrhea", Am Fam Physician, 71(2): 285-291, Jan. 15, 2005.

(56) References Cited

OTHER PUBLICATIONS

Harel., "Dysmenorrhea in adolescents and young adults: an update on pharmacological treatments and management strategies," Expert Opinion on Pharmacotherapy, vol. 13 No. 15, pp. 2157-2170, XP055389783, Sep. 18, 2012.
Harrington et al: "Cross-sectional association of endogenous steroid hormone, sex hormone-binding globulin, and precursor steroid levels with hemostatic factor levels in postmenopausal women", J Thromb Haemost., 15(1), p. 80-90, Jan. 1, 2017.
Hendrix and Alexander: "Primary dysmenorrhea treatment with a desogestrel-containing low-dose oral contraceptive", 66(6), p. 393-399, Dec. 1, 2002.
Kluft Cornelis et al: "Reduced hemostatic effects with drospirenone-based oral contraceptives containing estetrol vs ethinyl estradiol", Contraception, vol. 95, n° 2, p. 140-147, Sep. 1, 2016.
Kluft, "Effects on estrogenic and haemostatic variables of estetrol in combination with drospirenone," Presented at Eur. Soc. Contraception & Reprod. Health, 14th Cong, 2nd Global Conf., May 5, 2016.
Mawet et al: "Unique effects on hepatic function, lipid metabolism, bone and growth endocrine parameters of estetrol in combined oral contraceptives", Eur J Contracept Reprod Health Care, 20(6), p. 463-475, Jul. 27, 2015.
Odlind et al: "Can changes in sex hormone binding globulin predict the risk of venous thromboembolism with combined oral contraceptive pills?", Acta Obstet. Gynecol. Scand., 81(6), p. 482-490, Jun. 1, 2002.
Proctor and Farquhar: "Dysmenorrhoea", BMJ Clin Evid, 9, pii: 0813, Mar. 1, 2007.
Rosing et al: "Oral contraceptives and venous thrombosis: different sensitivities to activated protein C in women using second- and third-generation oral contraceptives", Br J Haematol., 97(1), p. 233-238, Apr. 1, 1997.
Shulman "Estelle®, Estetrol: changing hormones in advancing oral contraception," Presented at Eur. Soc. Contraception & Reprod. Health, 14th Cong, 2nd Global Conf., May 6, 2016.
Strowitzki et al., "Efficacy of ethinylestradiol 20 µg/drospirenone 3 mg in a flexible extended regimen in women with moderate-to-severe primiary dysmenorrhea: an open-label, multicenter, randomised, controlled study," J. Fam. Plann. Reprod. Health Care (2012) vol. 38, pp. 94-101, Mar. 27, 2012.
Sundell et al, "Factors influencing the prevalence and severity of dysmenorrhoea in young women.", Br J Obstet Gynaecol, 97(7), p. 588-594, Jul. 1, 1990.
Tchaicovski and Rosing: "Mechanisms of estrogen-induced venous thromboembolism", Thromb Res., 126(1):5-11, Feb. 16, 2010.
Winkler et al: "Cycle control, quality of life and acne with two low-dose oral contraceptives containing 20 microg ethinylestradiol", Contraception, 96(6), p. 469-476, Jun. 1, 2004.
Wong et al: "Oral contraceptive pill as treatment for pirmary dysmenorrhoea", Cochrane Database Syst Rev., CD002120, Apr. 15, 2009.
Ylikorkala and Dawood: "New concepts in dysmenorrhea", Am J Obstet Gynecol, 130(7), p. 833-847, Apr. 1, 1978.
Zhang and Wan Po: Efficacy of minor analgesics in primary dysmenorrhoea: a systematic review, Jul. 1, 1998.
Anderson and Spencer: "Risk factors for venous thromboembolism", Circulation, 107, I-9-I-16, Dec. 1, 2003.
Dinger et al: "Risk of venous thromboembolism and the use of dienogest- and drospirenone-containing oral contraceptives: results from a German case-control study", J Fam Plann Reprod Health Care, 36(3):123-129, Jul. 1, 2010.
Jick et al: "Risk of idiopathic cardiovascular death and nonfatal venous thromboembolism in women using oral contraceptives with differing progestagen components", Lancet, 346(8990): p. 1589-1593, Dec. 16, 1995.
Lidegaard et al: "Hormonal contraception and risk of venous trhomboembolism: national follow-study", BMJ, 339:b2890, Aug. 13, 2009.
Lidegaard et al: "Risk of venous thromboembolism from use of oral contraceptives containing different progestogens and oestrogen doses: Danish cohort study, 2001-9", BMJ, 343:d6423, Oct. 25, 2011.
Poort et al: "A common genetic variation in the 3'-untranslated region of the prothrombin gene is associated with elevated plasma prothrombin levels and an increase in venous thrombosis", Blood, 88(10), p. 3698-3703, Nov. 15, 1996.
Sidney et al: "Recent combined hormonal contraceptives (CHCs) and the risk of thromboembolism and other cardiovascular events in new users", Contraception, 87(1), p. 93-100, Jan. 1, 2013.
Spitzer et al: "Third generation oral contraceptives and risk of venous thromboembolic disorders: an international case-control study. Transnational Research Group on Oral Contraceptives and the Health of Young Women", BMJ, 312(7023), p. 83-88, Jan. 13, 1996.
Vlieg et al: "The venous thrombotic risk of oral contraceptives, effects of oestrogen dose and progestogen type: results of the MEGA case-control study", BMJ, 339:b2921, Aug. 13, 2009.
WTO: "Venous thromboembolic disease and combined oral contraceptives: results of international multicentre case-control study", Lancet, 346(8990): p. 1575-1582, Dec. 16, 1995.
Paul M. Fine: "Update on emergency contraception", Advances in Therapy, vol. 28, No. 2, p. 87-90 Dec. 10, 2010.
Erkkola et al: "Role of progestins in contraception", Acta Obstet Gynecol Scand., 84(3), pp. 207-216, Feb. 16, 2005.
Coelingh Bennink et al: "Estetrol (E4), the forgotten fetal steroid" 9th European Congress of Endocrinology Meeting Abstract No. S16,2, Endocrine Abstracts, vol. 14 2007.
Simoni et al: "The Discovery of Estrone, Estriol, and Estradiol and the Biochemical Study of Reproduction. The Work of Edward Adelbert Doisy", J. Biol. Chem., vol. 277, No. 28 e17, 2002.
Bull et al: "Synthesis and structure-activity studies of 8a- and 9beta-analogues of 14, 17-ethanoestradiol" J. Chem. Soc., Perkin Trans. 1, pp. 1003-1013, 2000.
Meulenbroeks et al: "21+7 day versus 24+4 day monophasic regimens of combined oral contraceptives for contraception (Protocol)", Cochrane database of systematic reviews, Issue 7, art. No: CD011781, 2015.
Dey et al., "Orodispersible tablets: A new trend in drug delivery," Journal of Natural Science, Biology, and Medicine, vol. 1, No. 1, p. 2-5, (Jul. 2010).
"Pharmaceutics of Biological Drugs," Zhao Yingzheng, ed., pp. 17-18, Zhejiang University Press (published on Jun. 30, 2011).
"Pharmaceutics," Liu Shubao,ed., p. 153, Henan Science and Technology Press (published on Jul. 31, 2007).
Office Action dated Mar. 16, 2020 in Chines Application No. 201680035626.3.
Office Action dated May 27, 2020 in U.S. Appl. No. 15/737,233 (US 2018-0185271).
Office Action dated Jul. 2, 2020 in U.S. Appl. No. 16/573,611 (US 2020-0046729).
Abot et al., "The uterine and vascular actions of estetrol delineate a distinctive profile of estrogen receptor α modulation, uncoupling nuclear and membrane activation," EMBO Mol Med (2014) vol. 6, No. 10, 1328-1346 (2014).
Alexander et al., "Why consider vaginal drug administration?" Fertility and Sterility, vol. 82, No. 1 (Jul. 2004).
Nillius et al., "Plasma Levels of Progesterone After Vaginal, Rectal, or Intramuscular Administration of Progesterone," American Journal of Obstetrics and Gynecology, vol. 110, No. 4 (1971).
Perie et al., "Controlling Drug Delivery," Pharmaceutics: Drug Delivery and Targeting pp. 8-9 (Pharm. Press, 2d ed., 2012).
Sarfaraz, "Handbook of Pharmaceutical Manufacturing Formulations Compressed Solid Products," Second edition, vol. 1, 2009.
U.S. Appl. No. 16/573,611, filed Sep. 17, 2019, Jost et al.
Notice of Allowance dated Jan. 7, 2020, in U.S. Appl. No. 16/025,719 (US 2019-0125759).
Office Action dated Dec. 6, 2019, in U.S. Appl. No. 16/573,611.
Office Action dated Feb. 3, 2020, in U.S. Appl. No. 16/573,611.
Alam et al., "Solid dispersions: a strategy for poorly aqueous soluble drugs and technology updates," Expert Opin. Drug Deliv. vol. 9, No. 11, pp. 1419-1440 (2012).

(56) References Cited

OTHER PUBLICATIONS

Ghandi et al., "BCS class IV drugs: Highly notorious candidates for formulation development," Journal of Controlled Release, vol. 248, pp. 71-95 (2017) (Available online Jan. 11, 2017).
Brenkova et al., CHISA 2006—17th International Congress of Chemical and Process Engineering.
Office Action dated Dec. 23, 2019, in Israeli Application No. 256283.
Office Action dated Feb. 11, 2020 in Colombian Application No. NC2017/0012766.
Office Action dated Feb. 18, 2020 in Indian Application No. 201817001353.
Office Action dated Feb. 6, 2020 in Chinese Application No. 201680035627.8.
Office Action dated Jan. 15, 2020, in Israeli Application No. 256282.
Office Action dated Mar. 19, 2019, in Colombian application No. NC2017/0012766.
Office Action dated May 19, 2020 in Israeli Application No. 256282.
Office Action dated May 19, 2020 in Israeli Application No. 256283.
Prince et al., "Phase II Clinical Study of BC-3781, a Pleuromutilin Antibiotic, in Treatment of Patients with Acute Bacterial Skin and Skin Structure Infections", Antimicrobial Agents and Chemotherapy, US, (May 2013), vol. 57, No. 5, doi:10.1128/AAC.02106-12, ISSN 0066-4804, pp. 2087-2094, XP055287601.
Strickley, R.G., "Solubilizing Excipients in Oral and Injectable Formulations," Pharmaceutical Research, Springer New York LLC, US, vol. 21, No. 2 (Feb. 1, 2004), doi:10.1023/B:PHAM.0000016235.32639.23, ISSN 0724-8741, pp. 201-230, XP009035738.
Tulchinsky D et al. "Plasma Estetrol as an Index of Fetal Well-being," Clin Edoctrinol Metab, vol. 40, pp. 560-567 (1975).

\* cited by examiner

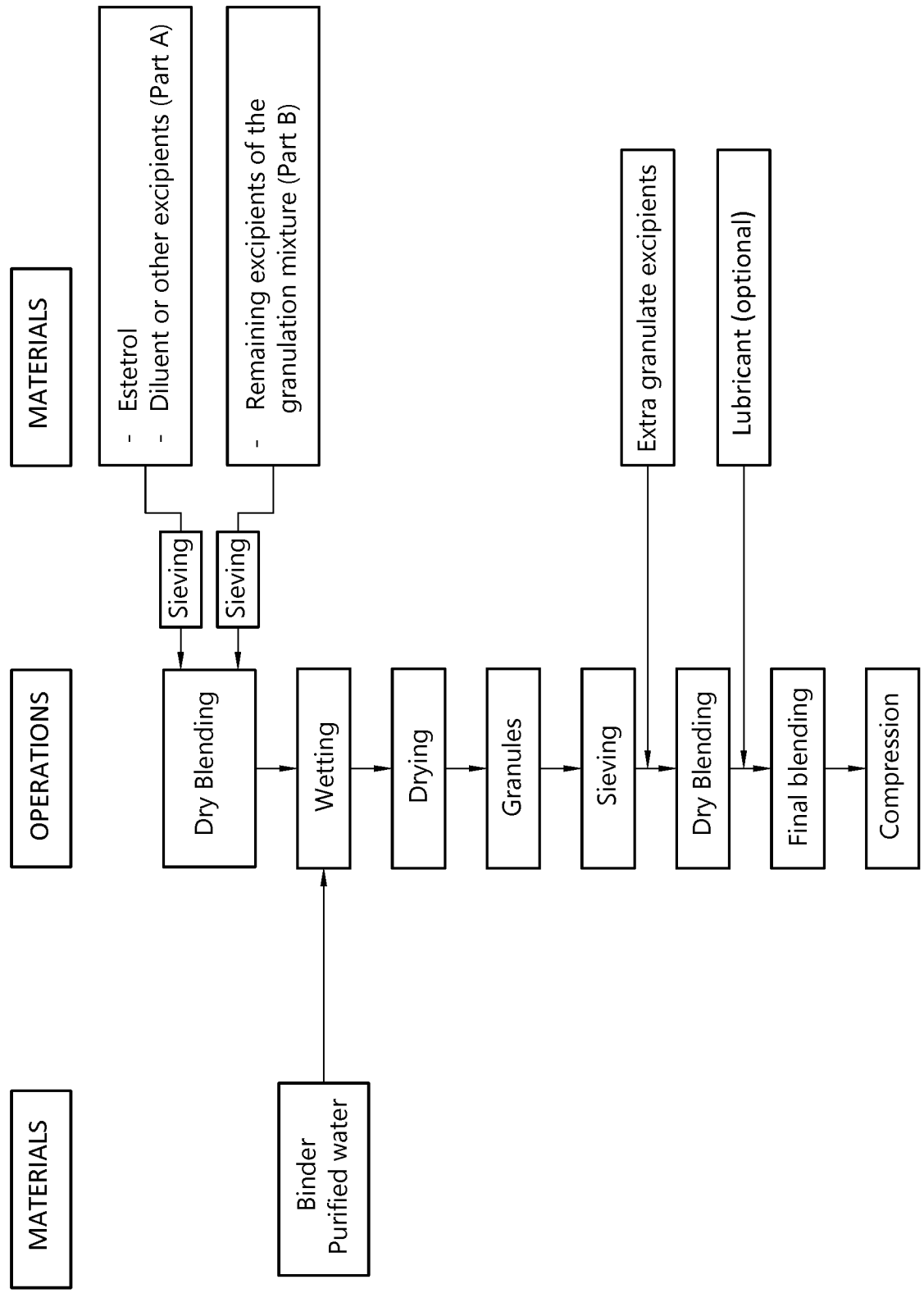

ORODISPERSIBLE DOSAGE UNIT CONTAINING AN ESTETROL COMPONENT

CROSS REFERENCE TO RELATED APPLICATIONS

This application is the U.S. National Stage of International Application PCT/EP2016/064065, filed Jun. 17, 2016, which claims priority from European Patent Application No. 15172767.4, filed Jun. 18, 2015.

TECHNICAL FIELD OF THE INVENTION

The present invention provides an orodispersible solid pharmaceutical dosage unit having a weight of 30-1,000 mg and containing at least 0.1 mg of an estetrol component selected from estetrol, estetrol esters and combinations thereof. This solid dosage unit consists of:
- 0.1-25 wt. % of estetrol particles containing at least 80 wt. % of the estetrol component; and
- 75-99.9 wt. % of one or more pharmaceutically acceptable ingredients.

The invention also provides a process of preparing the aforementioned solid dosage unit.

Furthermore, the invention relates to the use of the solid dosage unit in medical treatment, female hormone replacement therapy and female contraception, said use comprising sublingual, buccal or sublabial administration of the solid dosage unit.

BACKGROUND OF THE INVENTION

Estetrol is a human steroid, produced by the fetal liver during pregnancy only. This natural hormone was discovered in urine of pregnant women by Diczfalusy and coworkers in 1965. Estetrol has the structure of an estrogenic steroid with four hydroxyl groups. Estetrol is synthesized in the fetal liver from estradiol and estriol by the two enzymes 15α- and 16α-hydroxylase. After birth the neonatal liver rapidly loses its capacity to synthesize estetrol because these two enzymes are no longer expressed.

Estetrol reaches the maternal circulation through the placenta and was already detected at nine weeks of pregnancy in maternal urine. During the second trimester of pregnancy high levels were found in maternal plasma, with steadily rising concentrations of unconjugated estetrol to about 1 ng/mL (>3 nmol/L) towards the end of pregnancy. So far the physiological function of estetrol is unknown. The possible use of estetrol as a marker for fetal well-being has been studied quite extensively. However, due to the large intra- and inter-individual variation of maternal estetrol plasma levels during pregnancy this appeared not to be feasible.

Since 2001 estetrol has been studied extensively. In humans estetrol was shown to have a high and dose-proportional oral bioavailability and a long terminal elimination half-life of about 28 hours. Results from in vitro studies showed that estetrol binds highly selective to the estrogen receptors with preference for the ERα form of the receptor, unlike the estrogens ethinyl estradiol and 17β-estradiol. Also in contrast with ethinyl estradiol and especially with 17β-estradiol, estetrol does not bind to sex hormone binding globulin (SHBG) and does not stimulate the production of SHBG in vitro.

The properties of estetrol have also been investigated in a series of predictive, well validated pharmacological in vivo rat models. In these models, estetrol exhibited estrogenic effects on the vagina, the uterus (both myometrium and endometrium), body weight, bone mass, bone strength, hot flushes and on ovulation (inhibition). All these effects of estetrol were dose-dependent with maximum effects at comparable dose levels. Surprisingly, estetrol prevented tumour development in a DMBA mammary tumour model to an extent and at a dose level similar to the anti-estrogen tamoxifen and to ovariectomy. This anti-estrogenic effect of estetrol in the presence of 17β-estradiol has also been observed in in vitro studies using human breast cancer cells.

Buccal, sublingual or sublabial administration of estetrol is mentioned in a number of patent applications, including WO 2002/094275, WO 2002/094276, WO 2002/094278 and WO 2003/018026. Estetrol containing dosage units for buccal, sublingual or sublabial administration are not described in these publications.

WO 2010/033832 describes an oral dosage form comprising an estriol compound and a pharmaceutically acceptable matrix material, wherein the oral dosage form releases at least about 90% of the estriol compound in a time of less than about 300 seconds when contacted with saliva of the buccal and/or sublingual cavity.

US 2007/286829 describes an orally administered solid dosage form capable of delivering ethinyl estradiol with improved bioavailability, said solid dosage form comprising (i) about 0.5 μg to about 50 μg of ethinyl estradiol and (ii) an oral dissolution enhancing carrier that provides for at least 15% absorption of the ethinyl estradiol through the oral mucosa when said solid dosage form is orally administered to the patient with 2 ounces of water or less.

U.S. Pat. No. 6,117,446 describes a buccal dosage unit for administering a combination of steroidal active agents, comprising a compressed tablet of a bioerodible polymeric carrier and therapeutically effective amounts of an androgenic agent selected from testosterone and pharmacologically acceptable esters thereof, a progestin and an estrogen. The examples describe buccal dosage units that were prepared by thoroughly mixing the following components: estrogen, progestogen, androgen, polyethylene oxide, carbomer and magnesium stearate. Next, the mixture was granulated by means of fluid bed granulation and the granulate so obtained was pressed into tablets.

Oral dosage units containing estetrol have been described in several patent publications.

WO 2002/094276 describes a pharmaceutical composition for use in a method of hormone replacement therapy, which method comprises administering to a person in need of such a therapy an effective amount of estetrol, said composition containing virtually no progestogen or anti-progestin. WO 2002/094276 describes the preparation of estetrol tablets having a weight of 185 mg, containing 1.5 mg estetrol, on the basis of the following formulation:

|  | mg |
|---|---|
| Estetrol | 1.5 |
| Polyvinylpyrrolidone (Kollidon 25 ® ex BASF) | 12.5 |
| Lactose | 135.795 |
| Microcrystalline cellulose (Avicel PH 101 ®) | 26.25 |
| Glyceryl palmitostearate (Precirol ®) | 2.775 |
| Anhydrous colloidal silica (Aerosil 200 ®) | 1.0 |
| Crospovidone (Polyplasdone XL ®) | 4.0 |
| Coloring agent | 0.18 |

WO 2002/094275 describes the use of an estetrol in a method of increasing libido in a woman, said method comprising administering to said woman an effective amount of estetrol. Oral administration is mentioned as a suitable mode of administration. This patent application describes the same estetrol tablet as WO 2002/094276.

WO 2002/094279 describes the use of estetrol in a method of contraception in mammalian females, which method comprises the oral administration of said estrogenic component and a progestogenic component to a female of childbearing capability in an effective amount to inhibit ovulation. The following formulation for a 185 mg estetrol tablet is described in this international patent application.

|  | mg |
| --- | --- |
| Estetrol | 1.5 |
| Levonorgestrel | 0.15 |
| Polyvinylpyrrolidone (Kollidon 25 ® ex BASF) | 13.5 |
| Lactose | 135.645 |
| Microcrystalline cellulose (Avicel PH 101 ®) | 26.25 |
| Glyceryl palmitostearate (Precirol ®) | 2.775 |
| Anhydrous colloidal silica (Aerosil 200 ®) | 1.0 |
| Crospovidone (Polyplasdone XL ®) | 4.0 |
| Coloring agent | 0.18 |

WO 2003/041718 describes the use of estetrol in a method of hormone replacement in mammals, which method comprises the oral administration of estetrol and a progestogenic component to a mammal in an effective amount to prevent or treat symptoms of hypoestrogenism. This patent application describes the same estetrol tablet as WO 2002/094279.

WO 2007/081206 describes the use of estetrol in a method of treating an acute vascular disorder in a mammal, said method comprising orally administering to said mammal, upon demand, an effective amount of the estetrol to the mammal. This patent application describes the preparation of hard gelatine capsules, containing 100 mg estetrol and 25 mg sildenafil citrate per capsule.

WO 2008/156365 describes the use of estetrol in the treatment of Meconium Aspiration Syndrome (MAS) in a newborn infant, said treatment comprising administering an effective amount of estrogen to said newborn infant within 7 days after birth. The international patent application describes a suppository for use in newborn infants comprising at least 1 μg of estrogen, said suppository further being characterized by a maximum diameter of less than 10 mm and a weight of less than 0.5 g. The excipient contained in the suppository may be based on lipid material that melts at body temperature or it may be based on a hydrophilic component that dissolves or disintegrates when it comes into contact with water.

SUMMARY OF THE INVENTION

The present invention provides an orodispersible solid pharmaceutical dosage unit containing an estetrol component. The dosage unit rapidly releases the estetrol in aqueous environment. The solid dosage unit is easy to manufacture and perfectly suited for sublingual, buccal or sublabial administration. Sublingual, buccal and sublabial administration each offer the advantages that the estetrol component does not have to pass through the digestive system and avoids first-pass liver exposure. Furthermore, these modes of administration provide a rapid onset of action.

The solid dosage unit according to the present invention has a weight between 30 and 1,000 mg; contains at least 100 μg of an estetrol component selected from estetrol, estetrol esters and combinations thereof; and consists of:
- 0.1-25 wt. % of estetrol particles containing at least 80 wt. % of the estetrol component; and
- 75-99.9 wt. % of one or more pharmaceutically acceptable ingredients.

This solid dosage is obtainable by a process comprising:
providing estetrol particles containing at least 80 wt. % of the estetrol component and having a volume median diameter of 2 μm to 50 μm;
mixing the estetrol particles with one or more granulation excipients to produce a granulation mixture;
mixing the granulation mixture with a granulation liquid to produce estetrol-containing granules, said granulation liquid containing at least 60 wt. % of liquid solvent;
removing liquid solvent from the estetrol-containing granules to produce dry estetrol-containing granules;
optionally mixing the dry granules with one or more tabletting excipients; and
forming the dry granules or the mixture of the dry granules and the one or more tabletting excipients into a solid dosage unit.

Rapid and complete dissolution of the estetrol component into saliva is essential for efficient delivery of the component via sublingual, buccal or sublabial administration of the solid dosage unit. The inventors have unexpectedly found that the estetrol component is rapidly released and dispersed into saliva and absorbed through the mucosal lining of the oral cavity if it is present in the solid dosage unit in the form of very small particles.

The invention also provides a process of preparing the aforementioned solid dosage unit, said process comprising the steps of:
providing estetrol particles containing at least 80 wt. % of an estetrol component selected from estetrol, estetrol esters and combinations thereof and having a volume median diameter of 2 μm to 50 μm;
mixing the estetrol particles with one or more granulation excipients to produce a granulation mixture;
mixing the granulation mixture with a granulation liquid to produce estetrol-containing granules, said granulation liquid containing at least 60 wt. % of liquid solvent;
removing liquid solvent from the estetrol-containing granules to produce dry estetrol-containing granules;
optionally mixing the dry granules with one or more pharmaceutically acceptable excipients; and
forming the dry granules or the mixture of the dry granules and the one or more tabletting excipients into a solid dosage unit The production of the estetrol-containing granules in this process may suitably be carried out, for instance, in a high shear granulator, a low shear granulator or a fluidized bed granulator.

BRIEF DESCRIPTION OF THE FIGURE

FIG. 1 illustrates the manufacturing process flow chart used in Example 4.

DETAILED DESCRIPTION OF THE INVENTION

A first aspect of the invention relates to an orodispersible solid pharmaceutical dosage unit having a weight between 30 and 1,000 mg, said dosage unit consisting of:
- 0.1-25 wt. % of estetrol particles containing at least 80 wt. % of an estetrol component selected from estetrol, estetrol esters and combinations thereof; and
- 75-99.9 wt. % of one or more pharmaceutically acceptable ingredients;

the solid dosage unit comprising at least 100 μg of the estetrol component;
wherein the solid dosage unit can be obtained by a process comprising:
- providing estetrol particles containing at least 80 wt. % of the estetrol component and having a volume median diameter of 2 μm to 50 μm;
- mixing the estetrol particles with one or more granulation excipients to produce a granulation mixture;
- mixing the granulation mixture with a granulation liquid to produce estetrol-containing granules, said granulation liquid containing at least 60 wt. % of liquid solvent;
- removing liquid solvent from the estetrol-containing granules to produce dry estetrol-containing granules;
- optionally mixing the dry granules with one or more tabletting excipients; and
- forming the dry granules or the mixture of the dry granules and the one or more tabletting excipients into a solid dosage unit.

The term 'estetrol' as used herein refers to 1,3,5 (10)-estratrien-3,15α,16α,17β-tetrol or 15α-hydroxyestriol as well as hydrates of estetrol, e.g. estetrol monohydrate.

The term 'orodispersible dosage unit' as used herein refers to a dosage unit that is designed to rapidly disintegrate in the oral cavity when it comes into contact with saliva and to disperse the estetrol component into the saliva so it may be absorbed through the mucosal lining of the oral cavity.

The terms 'pharmaceutically acceptable ingredients' as used herein include both pharmaceutically acceptable excipients and pharmaceutically active ingredients other than the estetrol component, as further defined below.

The term 'sublingual' as used herein refers to the pharmacological route of administration by which the estetrol component diffuses into the blood through tissues under the tongue.

The term 'buccal' as used herein refers to the pharmacological route of administration by which the estetrol component diffuses into the blood through tissues of the buccal vestibule, the area inside the mouth between the lining of cheek (the buccal mucosa) and the teeth/gums.

The term 'sublabial' as used herein refers to the pharmacological route of administration by which the estetrol component is placed between the lip and the gingiva.

The term "granulation" as used herein, unless indicated otherwise, relates to a process in which primary powder particles are made to adhere to form larger, multiparticle entities called "granules".

The term 'tabletting excipient' as used herein refers to a pharmaceutically acceptable excipient that can be used in the manufacture of solid dosage units such as tablets.

Unless indicated otherwise, all percentages mentioned herein are percentages by weight.

Examples of solid dosage units encompassed by the present invention include tablets, dragees, lozenges and films. In accordance with a preferred embodiment, the dosage unit is a tablet, most preferably a compressed tablet.

The solid dosage unit typically has a weight between 40 and 500 mg, more preferably between 50 and 300 mg, and most preferably between 70 and 150 mg.

The solid dosage unit preferably comprises at least 1 wt. %, more preferably 2-25 wt. % and most preferably 2.2-15 wt. % of the estetrol component.

The amount of the estetrol component contained in the solid dosage unit preferably lies within the range of 0.3-100 mg, more preferably of 0.5-40 mg and most preferably of 1-20 mg.

The estetrol component of the present invention preferably is selected from the group consisting of estetrol, esters of estetrol wherein the hydrogen atom of at least one of the hydroxyl groups has been substituted by an acyl radical of a hydrocarbon carboxylic, sulfonic acid or sulfamic acid of 1-25 carbon atoms; and combinations thereof. Even more preferably, the estetrol component is estetrol (including estetrol hydrates). Most preferably, the estetrol component contained in the dosage unit is estetrol monohydrate.

The particle size of the estetrol particles in the solid dosage unit should be adequate for achieving sufficient absorption of the estetrol component after sublingual, buccal or sublabial administration. The estetrol particles within the solid dosage unit and (independently) the estetrol particles used in the preparation of the solid dosage unit preferably have a volume median diameter in the range of 3 μm to 35 μm, more preferably in the range of 4 μm to 25 μm and most preferably in the range of 5 μm to 15 μm.

The estetrol particles within the solid dosage unit and (independently) the estetrol particles used in the preparation of the solid dosage unit preferably contain not more than a limited amount of particles with a particle size in excess of 60 μm. Preferably, not more than 10 vol. % of more than 60 μm ($D_{90}$), more preferably not more than 5 vol. % of the estetrol particles have a particle size of more than 60 μm ($D_{95}$). Even more preferably, not more than 10 vol. % of more than 40 μm ($D_{90}$), more preferably not more than 5 vol. % of the estetrol particles have a particle size of more than 40 μm ($D_{95}$).

The particles size distribution of the estetrol particles, and of other particulate materials used in the present process, may suitably be determined by means of laser diffraction. The particle size distribution of the estetrol particles within the solid dosage unit can suitably be determined using spectroscopic techniques, e.g. Raman mapping.

The solid dosage unit of the present invention offers the advantage that the estetrol component is rapidly released when the dosage unit is introduced into the oral cavity and comes into contact with saliva. The rate of release of the estetrol component from the dosage unit can suitably be determined using the dissolution test described in the Examples, or a disintegration test according to Ph. Eur. 2.9.1 ("Disintegration of tablets and capsules") and USP <701> ("Disintegration"), also described in the Examples. The solid dosage unit of the present invention, when subjected to the aforementioned dissolution test, typically releases at least 50%, more preferably at least 70% and most preferably at least 80% of the estetrol component after 5 minutes. The solid dosage unit of the present invention, when subjected to the aforementioned disintegration test, typically disintegrates within less than 5 minutes, more preferably within less than 2 minutes, still more preferably within less than 1.5 minutes, still more preferably within less than 1 minute, still more preferably within less than 45 seconds, and most preferably within less than 30 seconds.

The estetrol particles employed in the solid dosage unit and in the present process preferably contain at least 90 wt. % of the estetrol component, more preferably at least 95 wt. % of the estetrol component and most preferably at least 99 wt. % of the estetrol component. Besides the estetrol component, the estetrol particles can suitably contain pharmaceutically acceptable excipients that aid dispersion of the dosage unit and dissolution and absorption of the estetrol component. Examples of such excipients include tensioactive agents, cosolvents, absorption enhancer, superdisintegrants and buffering agents.

The estetrol particles typically represent between 0.5-20 wt. % of the dosage unit. More preferably, the estetrol particles represent 1-18 wt. %, most preferably 5-15 wt. % of the dosage unit.

The solid dosage unit of the present invention preferably contains 50-99.8 wt. % of water-soluble carbohydrate selected from maltose, fructose, sucrose, lactose, glucose, galactose, trehalose, xylitol, sorbitol, erythritol, maltitol, mannitol, isomalt and combinations thereof. More preferably, the water-soluble carbohydrate is selected from lactose, mannitol, erythritol and combinations thereof. Even more preferably, the water-soluble carbohydrate is selected from mannitol, erythritol and combinations thereof. Most preferably, the water-soluble carbohydrate is mannitol.

The water-soluble carbohydrate is preferably contained in the dosage unit in crystalline form.

According to another preferred embodiment, the dosage unit contains 0.1-15 wt. %, more preferably 0.2-10 wt. % and most preferably 1-5 wt. % of a disintegrating agent selected from modified starches (e.g. sodium salt of carboxymethyl starch), crosslinked polyvinylpyrrolidone, crosslinked carmellose and combinations thereof.

The estetrol particles are present in the solid dosage unit of the present invention as a component of granules that additionally contain one or more granulation excipients.

The dry estetrol-containing granules typically constitute 20-99.9 wt. % of the oral dosage unit. More preferably, these granules represent 50-99.8 wt. %, most preferably 60-99.7 wt. % of the oral dosage unit.

Typically, the dry estetrol-containing granules that contain the estetrol particles have a volume median diameter of 100-4,000 μm, more preferably of 150-1,000 μm and most preferably of 200-600 μm.

The dry estetrol-containing granules typically comprise 70-95 wt. % of one or more granulation excipients and 5-30 wt. % of the estetrol component. Even more preferably, these granules comprise 75-90 wt. % of the one or more granulation excipients and 10-25 wt. % of the estetrol component.

Other granulation excipients that may suitably be incorporated into the estetrol-containing granules include water-soluble carbohydrate, diluents/fillers (e.g. calcium salts, microcrystalline cellulose), binders, disintegrating agents, mucoadhesive agents, flavouring, colouring, glidents, lubricants and combinations thereof.

The dry estetrol-containing granules preferably contain at least 20 wt. %, more preferably at least 35 wt. % and most preferably at least 45 wt. % of the water-soluble carbohydrate as defined herein before.

The dry estetrol-containing granules preferably contain at least 30%, more preferably at least 40% and most preferably at least 50% of the water-soluble carbohydrate by weight of the one or more granulation excipients.

The dry estetrol-containing granules typically contain 0-20 wt. % of the binder as defined herein before. Even more preferably these granules contain 0.1-15 wt. %, more preferably 0.2-10 wt. % of the binder.

In accordance with another preferred embodiment, the dry estetrol-containing granules comprise 0.1-20 wt. %, more preferably 0.2-10 wt. % of a disintegrating agent as defined herein before.

Besides dry estetrol-containing granules, the solid dosage unit of the present invention may suitably contain 0.1-80 wt. %, more preferably 0.2-50 wt. % and most preferably 0.3-40 wt. % of tabletting excipients selected from lactose, mannitol, xylitol, microcrystalline cellulose, starch, croscarmellose sodium, polyvinyl pyrrolidone and combinations thereof. According to one particularly preferred embodiment, the tabletting excipients comprises at least 50 wt. % mannitol. In accordance with another preferred embodiment, the tabletting excipients comprise at least 50 wt. % lactose.

The solid dosage unit may contain one or more other pharmaceutically active ingredients besides the estetrol component. Examples of such other pharmaceutically active ingredients include steroid hormones. The solid dosage unit of the present invention preferably contains 0.05-10 mg, more preferably 0.1-5 mg of one or more progestogens, preferably one or more progestogens selected from progesterone, levonorgestrel, norgestimate, norethisterone, norethisteron-acetate (NETA), dydrogesterone, drospirenone, 3-beta-hydroxydesogestrel, 3-keto desogestrel (=etonogestrel), 17-deacetyl norgestimate, 19-norprogesterone, acetoxypregnenolone, allylestrenol, anagestone, chlormadinone, cyproterone, demegestone, desogestrel, dienogest, dihydrogesterone, dimethisterone, ethisterone, ethynodiol diacetate, flurogestone acetate, gastrinon, gestodene, gestrinone, hydroxymethylprogesterone, hydroxyprogesterone, lynestrenol (=lynoestrenol), medrogestone, medroxyprogesterone, megestrol, melengestrol, nestorone, nomegestrol, nomegestrol-acetate (NOMAC), norethindrone (=norethisterone), norethynodrel, norgestrel (includes d-norgestrel and dl-norgestrel), norgestrienone, normethisterone, progesterone, quingestanol, (17alpha)-17-hydroxy-11-methylene-19-norpregna-4,15-diene-20-yn-3-one, tibolone, trimegestone, algestone acetophenide, nestorone, promegestone, 17-hydroxyprogesterone esters, 19-nor-17hydroxyprogesterone, 17alpha-ethinyl-testosterone, 17alpha-ethinyl-19-nor-testosterone, d-17beta-acetoxy-13beta-ethyl-17alpha-ethinyl-gon-4-en-3-one oxime and prodrugs of these compounds. Preferably the one or more progestogens used in accordance with the present invention is selected from the group consisting of progesterone, desogestrel, etonogestrel, gestodene, dienogest, levonorgestrel, norgestimate, norethisterone, norethisteron-acetate (NETA), nomegestrol, nomegestrol-acetate (NOMAC), drospirenone, trimegestone, nestorone and dydrogesterone.

The solid dosage unit according to the present invention preferably contains 0.05-100 mg, more preferably 0.1-50 mg of one or more androgens, preferably one or more androgens selected from testosterone, dehydroepiandrosterone (DHEA); DHEA-sulphate (DHEAS); testosterone esters (e.g. testosterone undecanoate, testosterone propionate, testosterone phenylpropionate, testosterone isohexanoate, testosterone enantate, testosterone bucanate, testosterone decanoate, testosterone buciclate); methyltestosterone; mesterolon; stanozolol; androstenedione; dihydrotestosterone; androstanediol; metenolon; fluoxymesterone; oxymesterone; methandrostenolol; MENT and prodrugs of these compounds. Most preferably the one or more androgens are selected from the group consisting of testosterone, DHEA and MENT.

Another aspect of the present invention relates to the use of the aforementioned solid dosage unit in medical treatment, in female hormone replacement therapy or in female contraception, said use comprising sublingual, buccal or sublabial administration of the dosage unit. Examples of medical treatment in which the solid dosage unit of the present invention may suitably be used include treatment of osteoporosis and estrogen add-back treatment in endometriosis, breast cancer or prostate cancer. In accordance with a preferred embodiment, the solid dosage unit is used in female hormone replacement therapy or female contraception. Most preferably, the solid dosage is used in female hormone replacement therapy, especially to treat vulvovaginal atrophy and/or vasomotor symptoms.

The use of the solid dosage unit in medical treatment, in female hormone replacement therapy or in female contraception, typically comprises sublingual, buccal or sublabial administration of the dosage unit to provide at least 0.1 mg, more preferably 0.5-100 mg and most preferably 1-40 mg of the estetrol component.

To treat vulvovaginal atrophy the dosage unit is preferably administered in an amount sufficient to provide at least 0.1 mg of the estetrol component. More preferably, the administered dosage unit provides at least 0.5 mg, most preferably at least 1 mg of the estetrol component. In the treatment of vulvovaginal atrophy the dosage unit is preferably administered in an amount that provides no more than 50 mg, more preferably not more than 20 mg and most preferably not more than 10 mg of the estetrol component.

To treat vasomotor symptoms the dosage unit is preferably administered in an amount sufficient to provide at least 0.2 mg of the estetrol component. More preferably, the administered dosage unit provides at least 1 mg, most preferably of at least 2 mg of the estetrol component. In the treatment of vasomotor symptoms the dosage unit is preferably administered in an amount that provides no more than 100 mg, more preferably not more than 40 mg and most preferably not more than 20 mg of the estetrol component.

Typically, these uses of the solid dosage unit comprise once daily administration of the dosage unit during a period of at least 1 week, more preferably of at least 2 weeks. During these periods the solid dosage unit is preferably administered to provide a daily dose of at least 0.05 mg, more preferably of 0.1-40 mg and most preferably of 0.2-20 mg of the estetrol component.

To treat vulvovaginal atrophy the dosage unit is preferably administered to provide a daily dose of at least 0.1 mg of the estetrol component. More preferably, the dosage unit is administered to provide a daily dose of 0.5-20 mg, most preferably of 1-10 mg of the estetrol component.

To treat vasomotor symptoms the dosage unit is preferably administered to provide a daily dose of at least 0.2 mg of the estetrol component. More preferably, the dosage unit is administered to provide a daily dose of 1-40 mg, most preferably 2-20 mg of the estetrol component.

Yet another aspect of the invention relates to a process of preparing a solid dosage unit as described herein before, said process comprising the steps of:
providing estetrol particles containing at least 80 wt. % of an estetrol component selected from estetrol, estetrol esters and combinations thereof and having a volume median diameter of 2 µm to 50 µm;
mixing the estetrol particles with one or more granulation excipients to produce a granulation mixture;
mixing the granulation mixture with a granulation liquid to produce estetrol-containing granules, said granulation liquid containing at least 60 wt. % of liquid solvent;
removing liquid solvent from the estetrol-containing granules to produce dry estetrol-containing granules;
optionally mixing the dry granules with one or more tabletting excipients; and
forming the dry granules or the mixture of the dry granules and the one or more tabletting excipients into a solid dosage unit.

In the present process the granulation mixture is preferably produced by combining the estetrol particles with the one or more granulation excipients in a weight ratio that is in the range of 1:2 to 1:1000, more preferably in the range of 1:3 to 1:100 and most preferably in the range of 1:4 to 1:10.

The one or more granulation excipients used in the preparation of the granulation mixture preferably include water-soluble carbohydrate as defined herein before. Preferably, said water-soluble carbohydrate constitutes at least 50 wt. %, more preferably at least 60 wt. % and most preferably at least 80 wt. % of the one or more granulation excipients.

The one or more granulation excipients of the granulation mixture preferably include 0.1-20 wt. %, more preferably 0.15-10 wt. % and most preferably 0.2-5.0 wt. % of binder as defined herein before; all percentage calculated by weight of the granulation mixture.

The one or more granulation excipients of the granulation mixture may suitably include a disintegrating agent as defined herein before. Preferably, the disintegrating agent constitutes 0.1-20 wt. %, more preferably 0.2-10 wt. % of the granulation mixture.

The estetrol-containing granules are preferably produced by mixing the granulation mixture with the granulation liquid in a weight ratio that is in the range of 0.5:1 to 20:1. Even more preferably, the granulation mixture and the granulation liquid are mixed in a weight ratio that is in the range of 0.8:1 to 12:1, even more preferably in the range of 1:1 to 10:1 and most preferably of 1.5:1 to 5:1. The aforementioned weight ratio is calculated on the basis of the total amount of granulation mixture and granulation liquid that is used in the preparation of the dry estetrol-containing granules.

The estetrol-containing granules are preferably produced by mixing the granulation mixture with the granulation liquid in a high shear granulator, a low shear granulator or a fluidized bed granulator. Most preferably, the granules are prepared in a low shear granulator.

The granulation liquid employed in the present process preferably contains at least 60 wt. %, more preferably at least 80 wt. % and most preferably at least 90 wt. % of polar solvent selected from water, methanol, ethanol, iso-propanol, acetone and combinations thereof.

According to a particularly preferred embodiment, the granulation liquid contains at least 60 wt. %, more preferably at least 80 wt. % and most preferably at least 90 wt. % of polar solvents selected from water, ethanol and combinations thereof. The polar solvent employed in the granulation liquid preferably contains at least 80 wt. % water, more preferably at least 90 wt. % water.

The granulation liquid employed in the present process may suitably contain further excipients besides liquid solvent. Examples of such further excipients include binders, disintegrating agents, mucoadhesive agents, colouring, flavouring and combinations thereof.

Preferably, the granulation liquid contains 0.5-40 wt. %, more preferably 1-25 wt. % and most preferably 2-20 wt. % of binder, said binder being selected from cellulose derivatives, starch and starch derivatives (e.g. pregelatinized starch), polyvinyl alcohol (PVA), polyvinylpyrrolidone (PVP), agar, gelatin, guar gum, gum Arabic, alginate, polyethylene glycol (PEG), glucose, sucrose, sorbitol and combinations thereof. Preferably, the binder employed in the present process is selected from cellulose derivatives, pregelatinized starch, polyvinylpyrrolidone and combinations thereof.

Examples of cellulose derivatives that may be employed in the dosage unit as binder include hydroxypropyl cellulose, hydroxyethyl cellulose, hydroxymethyl cellulose, hydroxypropylmethylcellulose, methylcellulose, ethylcellulose, carboxymethyl cellulose and combinations thereof.

In the present process liquid solvent is preferably removed after the mixing of the granulation mixture with the granulation liquid has been completed. In a preferred embodiment reduced pressure is applied (e.g. less than 200 mbar) to facilitate the removal of liquid solvent during production of the estetrol-containing granules. Typically, the liquid solvent is removed at elevated temperature (e.g. >50° C.).

The dry estetrol-containing granules produced in the present process typically have a volume median diameter in the range of 100-4,000 μm. More preferably, the volume median diameter of these granules is in the range of 200-1,000 μm, most preferably in the range of 200-600 μm.

Examples of the one or more tabletting excipients that are optionally combined with the dry estetrol-containing granules before the forming of the solid dosage unit include lactose, mannitol, xylitol, microcrystalline cellulose, starch, croscarmellose sodium, polyvinyl pyrrolidone and combinations thereof.

Preferably, in the present process the dry estetrol-containing granules are mixed with the one or more tabletting excipients in a weight ratio that is the range of 1:4 to 9:1, more preferably in the range of 1:2.5 to 3:1 and most preferably of 1:1.5 to 1.5 to 1.

In the present process the solid dosage unit may suitably be formed by direct compression or compression moulding. Most preferably, the solid dosage unit is formed by direct compression.

The solid dosage units obtained by the present method can be packaged in different ways. Preferably, the dosage units are packaged in a blister pack containing at least 14 dosage units.

The invention is further illustrated by means of the following non-limiting examples.

EXAMPLES

Dissolution Test

The dissolution test described below can be used to study the dissolution behaviour of orodispersible dosage units.

Dissolution Apparatus

Paddle and basket dissolution tester VanKel VK 7010 or VK 7025, autosampler VK 8000, 1000 mL dissolution vessels and porous micron filters (35 pin)

Dissolution Medium

Transfer 9,000 ml of demineralised water into a volumetric flask of 10,000 ml.

Add 68.05 g of $KH_2PO_4$ and 8.96 g NaOH and stir the solution until everything is dissolved.

Mix the solution and adjust the pH to 6.8 with NaOH or phosphoric acid, if necessary and make up to volume with demineralised water.

Dissolution Procedure

Transfer 900 ml of Dissolution Medium into each vessel of the paddle apparatus.

Assemble the apparatus, warm the medium to 37±0.5° C., and remove the thermometer.

Place in each of the six vessels one tablet at the bottom before starting the rotation of the paddles.

Start the rotation of the paddles immediately.

Use a stirring speed of 50 rpm.

Take samples of 5 ml from the dissolution vessels after 5, 10, 20, 30, 45, 60, 75 and 90 minutes for a complete dissolution profile. Take the sample from a position midway between the surface of the dissolution medium and the top of the paddle blade and not less than 10 mm from the vessel wall. The removed dissolution volume is not replaced by fresh dissolution medium.

Estetrol concentrations in the samples were determined by means of HPLC using estetrol stock solutions as a reference.

Preparation of Mobile Phase (MP) Phosphate Buffer

Transfer 1.15 g of $NH_4H_2PO_4$ (10 mM) into a 1,000 ml of demineralised water, dissolve it and adjust the pH to 3.0 with phosphoric acid.

HPLC Apparatus

Alliance 2695 Separations module consisting of a quaternary solvent delivery system, a variable volume injector, a temperature controlled autosampler, column thermostat and Photodiode array detector 2996 (all by Waters)

Analytical colunm: Symmetry C18, 3.9×150 mm, dp=5 μm (ex Waters)

Guard column: Security guard columg C18, 4×3 mm (Phenomenex)

Flow: 1.0 mL/min

Detection: UV @ 280 nm

Column temperature: 30° C.

Autosampler temperature: 10° C.

Injection volume: 100 μL

Run time: 12 min

Elution Gradient

| Time (min) | Acetonitrile (%) | Phosphate buffer (%) |
|---|---|---|
| 0 | 20 | 80 |
| 9 | 75 | 25 |
| 10 | 20 | 80 |
| 12 | 20 | 80 |

The dissolution tests are conducted in triplicate.

Particle Size Measurements

Particle size distribution of estetrol monohydrate is performed using a MALVERN MASTERSIZER MICROPLUS laser particle size analyzer.

Preparation of Dispersion Medium:

Weigh 1 g of estetrol monohydrate and 1 g of sorbitan trioleate into a flask.

Add 1 litre of n-hexane and mix for at least 1 hour at room temperature

Filter through a 0.45 μm filter.

Sample Preparation:

Put 100 mg of sample in a 25 mL beaker.

Add some drops of dispersion medium.

Mix carefully with a glass rod to suspend well the powder.

Add 10 mL of dispersion medium.

Perform the analysis with the sample dispersion unit's speed at 3000-3500 rpm.

Analysis:

Particle size measurements are performed three times using the same dispersion. The final result is obtained by averaging the results of the three determinations.

Example 1

A sublingual tablet is prepared by means of the procedure described below.

A granulation mixture having the composition shown in Table 1 is prepared by dry blending of the ingredients.

TABLE 1

| Ingredients | Wt. % |
| --- | --- |
| Milled estetrol [1] | 25 |
| Mannitol | 40 |
| Lactose | 35 |

[1] $D(v; 0.5)$ = appr. 15 μm

A granulation liquid having the composition shown in Table 2 is prepared by dispersing the pregelatinized starch into the water

TABLE 2

| Ingredients | Wt. % |
| --- | --- |
| Pregelatinized starch | 2 |
| Purified water | 98 |

The granulation mixture is granulated in a high shear granulator by gradually adding the aqueous granulation liquid. The total amount of granulation liquid added amounts to 25% by weight of the granulation mixture.

The granulate so obtained is dried in a vacuum drying oven at 40° C. and subsequently screened over a 500 μm sieve.

A tabletting mixture having the composition shown in Table 3 is prepared by mixing the dry granulate with the excipients for 15 minutes (except magnesium stearate). Magnesium stearate is added and mixing is continued for an additional 5 minutes.

TABLE 3

| Ingredients | Wt. % |
| --- | --- |
| Granulated estetrol | 50 |
| Lactose | 10 |
| Ludiflash ® [2] | 38.5 |
| Magnesium stearate | 1.5 |

[2] A mixture of mannitol (90 wt. %), crospovidone (5 wt. %) and polyvinyl acetate (5 wt. %)

The tabletting mixture is compressed into 80 mg round tablets with a diameter of 6.5 mm. The estetrol content of these tablets is 10 mg.

Example 2

A sublingual tablet is prepared by means of the procedure described below.

A granulation mixture having the composition shown in Table 4 is prepared by dry blending of the ingredients.

TABLE 4

| Ingredients | Wt. % |
| --- | --- |
| Milled estetrol [1] | 25 |
| Lactose | 75 |

[1] $D(v; 0.5)$ = appr. 15 μm

A granulation liquid having the composition shown in Table 5 is prepared by dispersing the polyvinylpyrrolidone (PVP) into the water.

TABLE 5

| Ingredients | Wt. % |
| --- | --- |
| PVP (polyvinylpyrrolidone) | 3 |
| Purified water | 97 |

The granulation mixture is granulated in a low shear granulator by gradually adding the granulation liquid. The total amount of granulation liquid added amounts to 25% by weight of the granulation mixture.

The granulate so obtained is dried in the low shear granulator at 40° C. and is subsequently screened over a 500 μm sieve.

A tabletting mixture having the composition shown in Table 6 is prepared by mixing the dry granulate with the excipients for 15 minutes (except magnesium stearate). Magnesium stearate is added and mixing is continued for an additional 5 minutes.

TABLE 6

| Ingredients | Wt. % |
| --- | --- |
| Granulated estetrol | 50 |
| Mannitol | 43.5 |
| Crospovidone | 5 |
| Magnesium stearate | 1.5 |

The blend is compressed into 80 mg round tablets with diameter 6.5 mm. The estetrol content of these tablets is approximately 10 mg.

Example 3

A sublingual tablet is prepared using the procedure described below.

A granulation mixture having the composition shown in Table 7 is prepared by dry blending of the ingredients.

TABLE 7

| Ingredients | Wt. % |
| --- | --- |
| Milled estetrol [1] | 25 |
| Lactose | 75 |

[1] $D(v; 0.5)$ = appr. 15 μm

A granulation liquid having the composition shown in Table 8 is prepared by dispersing the hydroxypropyl cellulose (HPC) into the water.

TABLE 8

| Ingredients | Wt. % |
| --- | --- |
| HPC (hydroxypropyl cellulose) | 2 |
| Purified water | 97 |

The granulation mixture is granulated in a fluid bed granulator by gradually adding the granulation liquid. The total amount of granulation liquid added amounts to 35% by weight of the granulation mixture.

The granulate so obtained is dried in the fluid bed granulator at 50° C. and subsequently screened over a 500 μm sieve.

A tabletting mixture having the composition shown in Table 9 is prepared by mixing the dry granulate with the excipients in Table 9 for 15 minutes (except magnesium stearate). Magnesium stearate is added and mixing is continued for an additional 5 minutes.

TABLE 9

| Ingredients | Wt. % |
| --- | --- |
| Granulated estetrol | 50 |
| Mannitol | 43.5 |
| Sodium starch glycolate | 5 |
| Magnesium stearate | 1.5 |

The blend is compressed into 80 mg round tablets with diameter 6.5 mm. The estetrol content of these tablets is approximately 10 mg.

Example 4

Seven different sets of sublingual tablets (formulations A to G) were prepared by means of the procedure described below and illustrated in FIG. 1.

The target amounts of estetrol per tablet were as follows: 100 μg for formulation A, 250 mg for formulation B, 7.5 mg for formulation C, 1 mg for formulation D, and 10 mg for formulations E, F and G.

The target weights for the tablets were as follows: 30 mg for formulations A and C, 1000 mg for formulations B and D, and 80 mg for formulations E, F and G.

The estetrol was mixed with a part of the main diluent and screened over a 800 μm screen. All other excipients were also screened over a 800 μm screen.

A binder solution of 10% PVP (polyvinylpyrrolidone) in demineralized water was prepared (the PVP concentration in the binder solution used for formulations B, C and F was 15%).

Granulation was started by adding the binder solution to the dry mixture consisting of the intragranular excipients (with a batchsize of ±100 gram). A granulate was formed after 30 seconds of mixing, and subsequently pure demineralized water was added until a suitable granulate was formed (as detected visually, 1 minute of granulation in total).

The granulate was dried overnight in a vacuum oven at 40° C. and subsequently milled over a 800 μm screen. The mixture thus obtained was mixed for 15 minutes with the extragranular excipients (except for magnesium stearate). Finally, magnesium stearate was added and mixed for 3 minutes.

Compression was executed using a single punch machine equipped with proper punches (5 mm punch for 30 mg tablets (A and C), 6 mm for 80 mg tablets (E, F and G) and 15 mm for 1000 mg tablets (B and D)).

Disintegration time was quantified according to the known protocol described in Ph. Eur. 2.9.1 ("Disintegration of tablets and capsules"), and in USP <701>("Disintegration") using water as the specified liquid.

Hardness was measured using the known protocol described in Ph. Eur. 2.9.8 ("Resistance to crushing of tablets").

The final formulations and corresponding tablet results can be found in Tables 10 and 11 below.

No problems were detected during the experiments, flowability of the blend was good and no sticking was observed.

TABLE 10 details of the formulations in Wt. %

| | Formulation # | | | | | | |
| --- | --- | --- | --- | --- | --- | --- | --- |
| | A | B | C | D | E | F | G |
| Intragranular | | | | | | | |
| Milled Estetrol [1] | 0.33 | 24.92 | 25.00 | 0.10 | 12.49 | 12.48 | 12.49 |
| Mannitol | 91.17 | 65.89 | 65.49 | 91.90 | 79.25 | 18.99 | |
| PVP (polyvinylpyrrolidone) | 2.00 | 2.99 | 3.00 | 2.00 | 2.01 | | 1.46 |
| Pregelatinized starch | | | | | | 1.01 | |
| Crospovidone | 4.01 | 4.00 | 4.00 | 4.00 | 4.00 | | |
| Lactose | | | | | | 17.51 | 36.04 |
| Demineralized water (per 100 gram granulation mixture) | 22 | 26 | 26 | 23 | 19 | 16 | 24 |
| Extragranular | | | | | | | |
| Crospovidone | 0.99 | 1.10 | 1.00 | 1.01 | 0.99 | | 5.00 |
| Lactose | | | | | | 10.01 | |
| Ludiflash ®[2] | | | | | | 38.49 | |
| Mannitol | | | | | | | 43.49 |
| Magnesium stearate | 1.49 | 1.10 | 1.50 | 0.99 | 1.25 | 1.50 | 1.52 |

[1] $D_{(v; 0.5)}$ = 15 μm
[2] Containing mannitol (90 wt. %), crospovidone (5 wt. %) and polyvinyl acetate (5 wt. %)

TABLE 11 experimentally determined characteristics of the Tablets

| | Test (average result of 6 samples) | | |
| --- | --- | --- | --- |
| Formulation # | Disintegration time (min:sec) | Hardness (N) | Weight (mg) |
| A | 0:39 | 14.17 | 28.2 |
| B | 1:44 | 85.85 | 1058.6 |
| C | 1:05 | 28.46 | 30.1 |
| D | 0:40 | 66.74 | 1048.9 |
| E | 0:32 | 29.70 | 78.9 |
| F | 0:41 | 30.97 | 82.2 |
| G | 0:33 | 22.69 | 78.1 |

It can be seen that all tablets were obtained with a final weight close to their target weight and that the disintegration times, even for the largest 1 g tablets, were very short, in accordance with the intended sublingual, buccal or sublabial administration route for these tablets.

Finally, the hardness of all tablets was within a very acceptable range.

Example 5

A randomized, open-label, two-period, cross-over, pharmacokinetic study is conducted to compare sublingual bioavailability of 10 mg estetrol administered in one 80 mg tablet (having the same composition as the tablets described in Example 4, Formulation E) with oral availability of estetrol contained in a 83 mg tablet containing 10 mg estetrol. These tablets are administered sublingually and orally to healthy female volunteers under fasting conditions.

Ten healthy female subjects are selected on the basis of the following criteria: age of 45-65 years (inclusive), non-smokers or past smokers (at least 6 months before dosing), body-mass index (BMI)=18.5 to 30 kg/m² (inclusive at the time of the screening).

At the start of the first and the second period of the study, between 07:00 am and 07:28 am, 5 subjects receive a single dose of the sublingual formulation of estetrol by administering one estetrol tablet (tablet weight 80 mg; 10 mg estetrol) and 5 subjects receive a single oral dose of the oral estetrol formulation by administering one estetrol tablet (tablet weight 83 mg; 10 mg estetrol), ingested together with 200 ml water.

Subjects are required to fast for at least 10 hours prior to tablet administration and for at least 4 hours after administration. Drinking of water or beverages is not permitted within 1 hour before the drug administration. Subjects receive 200 ml of water 1 hour prior to and 2 hours after tablet administration. Subjects are free to drink water and fruit tea from 4 hours following the tablet administration. Standardized meals are provided 10.5 hours before and 4, 6, 9, and 13 hours after tablet administration.

The sequence of events that occurs during the first and second period is shown in Table 12:

TABLE 12

| Event | |
|---|---|
| First period | |
| Day 1 | Confinement from 19:00 |
| Day 2 | Dosing, blood and urine sampling, confinement |
| Day 3 | Exit procedure, confinement till 8 am |
| Days 4-8 | Return visits |
| Days 9-13 | Wash out |
| Second period | |
| Day 14 | Confinement from 19:00 |
| Day 15 | Dosing, blood and urine sampling, confinement |
| Day 16 | Exit procedure, confinement till 8 am |
| Days 17-21 | Return visits |
| Days 22-26 | Wash out |
| Day 27 | Administration of a progestin |
| Day 28 | Phone call, progestin withdrawal test check |

The blood and urine sampling schedule used in this study is shown in Table 13.

TABLE 13

| Blood sampling | Blood collection (4 ml) is performed prior to administration of the tablet (0), and subsequently 0:10, 0:15, 0:20, 0:25, 0:30, 0:35, 0:40, 0:45, 0:50, 0:55, 1:00, 1:10, 1:20, 1:30, 2, 3, 4, 6, 10, 16, 24, 48, 72, 96, 120, 144 hours after administration. Total number of blood collections in each period is 27. |
|---|---|
| Urine sampling | Urine collection is performed prior to administration of the tablet and 2, 4, 8, 12, 24, 48, 72, 96, 120 and 144 hours after administration. Total number of urine collections in each period is 11. |

The estetrol concentration in the collected blood samples is determined by means of HPLC/MS/MS. The concentrations of glucuronided estetrol (D-ring) in the urine samples is also determined with the help of HPLC/MS/MS.

Results of these analyses show that the bioavailability of sublingually administered estetrol is comparable or even superior to orally administered estetrol. Furthermore, the data suggest that sublingually administered estetrol has an earlier bioavailability compared to orally administered estetrol. Sublingual estetrol has less impact on a liver function parameter.

The invention claimed is:

1. A process of making an orodispersible solid pharmaceutical dosage unit having a weight between 30 and 1,000 mg and containing at least 100 μg of an estetrol component selected from one or more of estetrol and estetrol esters, wherein the dosage unit consists of (i) 0.1-25 wt % estetrol particles, wherein the estetrol particles comprise the estetrol component in an amount of at least 80 wt. % of the particles and (ii) 75-99.9 wt. % of one or more pharmaceutically acceptable ingredients, the process comprising:
   providing estetrol particles having a volume median diameter of from 2 μm to 50 μm and comprising the estetrol component in an amount of at least 80 wt. % of the estetrol particles;
   mixing the estetrol particles with one or more granulation excipients to produce a granulation mixture;
   mixing the granulation mixture with a granulation liquid to produce estetrol-containing granules, wherein the granulation liquid comprises a liquid solvent in an amount of at least 60 wt. %;
   removing liquid solvent from the estetrol-containing granules to produce dry estetrol-containing granules;
   optionally, mixing the dry granules with one or more tabletting excipients to produce a mixture; and
   forming the dry granules or the mixture into a solid dosage unit having a weight between 30 and 1,000 mg and containing at least 100 μg of the estetrol component, wherein the estetrol particles make up 0.1-25 wt. % of the dosage unit.

2. The process according to claim 1, wherein the estetrol particles have a volume median diameter of 3-35 μm.

3. The process according to claim 1, wherein the granulation mixture contains a disintegrating agent in an amount of 0.1-20 wt. % selected from one or more of modified starches, crosslinked PVP, and crosslinked carmellose.

4. The process according to claim 1, wherein the granulation mixture is produced by combining the estetrol particles with the one or more granulation excipients in a weight ratio that is in a range of from 1:4 to 1:1,000.

5. The process according to claim 1, wherein the estetrol-containing granules are produced by mixing the granulation mixture with the granulation liquid in a weight ratio that is in a range of from 0.5:1 to 20:1.

6. The process according to claim 1, wherein the estetrol-containing granules are produced by mixing the granulation mixture with the granulation liquid in a high shear granulator, a low shear granulator, or a fluidized bed granulator.

7. The process according to claim 1, wherein the granulation liquid contains a polar solvent in an amount of at least 60 wt. % selected from one or more of water, methanol, ethanol, isopropanol, and acetone.

8. The process according to claim 1, wherein the granulation liquid contains a polar solvent in an amount of at least 60 wt. % selected from one or more of water and ethanol.

9. The process according to claim 7, wherein the polar solvent contains at least 80 wt. % water.

10. The process according to claim 1, wherein the granulation liquid contains a binder in an amount of 0.2-50 wt. % selected from one or more of cellulose derivatives, starch, starch derivatives, polyvinyl alcohol, polyvinylpyrrolidone, agar, gelatin, guar gum, gum Arabic, alginate, polyethylene glycol, glucose, sucrose, and sorbitol.

11. The process according to claim 10, wherein the binder is selected from one or more of cellulose derivatives, pregelatinized starch, and polyvinylpyrrolidone.

12. The process according to claim 10, wherein the binder comprises a cellulose derivative selected from one or more of hydroxypropyl cellulose, hydroxyethyl cellulose, hydroxymethyl cellulose, hydroxypropylmethylcellulose, methylcellulose, ethylcellulose, and carboxymethyl cellulose.

13. The process according to claim 1, wherein the dry estetrol-containing granules have a volume median diameter in a range of from 100 to 4,000 µm.

14. The process according to claim 1, wherein the one or more tabletting excipients comprise one or more of lactose, mannitol, xylitol, microcrystalline cellulose, starch, croscarmellose sodium, and polyvinyl pyrrolidone.

15. The process according to claim 1, wherein the solid dosage unit is formed by direct compression or compression molding.

16. The process according to claim 1, wherein the dosage unit has a weight between 40 mg and 500 mg.

17. The process according to claim 1, wherein the dosage unit contains the estetrol component in an amount of 0.5-25 wt. % of the dosage unit.

18. The process according to claim 1, wherein the dosage unit contains 0.3-100 mg of the estetrol component.

19. The process according to claim 1, wherein the estetrol component is estetrol.

20. The process according to claim 1, wherein the dosage unit contains a water-soluble carbohydrate in an amount of 50-99.9 wt. %, selected from one or more of maltose, fructose, sucrose, lactose, glucose, galactose, trehalose, xylitol, sorbitol, erythritol, maltitol, mannitol, and isomalt.

21. The process according to claim 20, wherein the dosage unit contains at least 20 wt. % mannitol.

22. The process according to claim 1, wherein the dosage unit contains a disintegrating agent in an amount of 0.1-20 wt. %, selected from one or more of modified starches, crosslinked polyvinylpyrrolidone, and crosslinked carmellose.

* * * * *